(12) United States Patent
Hajizadeh et al.

(10) Patent No.: US 7,045,297 B2
(45) Date of Patent: May 16, 2006

(54) RAPID PRION-DETECTION ASSAY

(75) Inventors: Kiamars Hajizadeh, Buffalo Grove, IL (US); Zakir S. Murtaza, Arlington Heights, IL (US)

(73) Assignee: Prion Developmental Laboratories, Inc., Buffalo Grove, IL (US)

( * ) Notice: Subject to any disclaimer, the term of this patent is extended or adjusted under 35 U.S.C. 154(b) by 194 days.

(21) Appl. No.: 09/993,391

(22) Filed: Nov. 14, 2001

(65) Prior Publication Data

US 2006/0024767 A1  Feb. 2, 2006

(51) Int. Cl.
*G01N 33/53* (2006.01)
(52) U.S. Cl. ............... 435/7.1; 435/7.94; 435/962; 435/970; 436/518; 436/524
(58) Field of Classification Search .............. 435/7.1, 435/7.92, 7.94, 970, 287.2, 962; 436/518, 436/501, 524, 528, 807, 164; 422/56
See application file for complete search history.

(56) References Cited

U.S. PATENT DOCUMENTS

| | | | |
|---|---|---|---|
| 5,141,850 A | 8/1992 | Cole et al. | |
| 5,248,619 A | 9/1993 | Skold et al. | 436/514 |
| 5,565,186 A | 10/1996 | Prusiner et al. | 424/9.2 |
| 5,737,061 A | 4/1998 | Sinclair et al. | 351/246 |
| 5,763,740 A | 6/1998 | Prusiner et al. | 800/2 |
| 5,792,901 A | 8/1998 | Prusiner et al. | 800/2 |
| 5,846,754 A * | 12/1998 | Pugia et al. | 435/23 |
| 5,891,641 A | 4/1999 | Prusiner et al. | |
| 5,922,533 A * | 7/1999 | Vallari et al. | 435/5 |
| 5,998,149 A | 12/1999 | Hsich et al. | 435/7.1 |
| 6,020,537 A | 2/2000 | Prusiner | |
| 6,096,563 A | 8/2000 | Hajizadeh et al. | 436/523 |
| 6,150,172 A | 11/2000 | Schmerr et al. | 435/975 |
| 6,165,784 A | 12/2000 | O'Rourke et al. | 435/326 |
| 6,166,187 A | 12/2000 | Prusiner et al. | 530/419 |
| 6,180,417 B1 | 1/2001 | Hajizadeh et al. | 436/518 |
| 6,197,207 B1 | 3/2001 | Chapman et al. | 210/767 |
| 6,214,565 B1 | 4/2001 | Prusiner et al. | 435/7.1 |
| 6,214,628 B1 | 4/2001 | Lakowicz et al. | 436/518 |
| 6,217,521 B1 | 4/2001 | Pomfrett | 600/484 |
| 6,221,614 B1 | 4/2001 | Prusiner et al. | 435/7.1 |
| 6,534,036 B1 | 3/2003 | Collinge et al. | |
| 6,716,641 B1 * | 4/2004 | Sundrehagen | 436/514 |
| 6,765,088 B1 | 7/2004 | Korth et al. | |
| 2002/0004246 A1 * | 1/2002 | Daniels et al. | 436/514 |
| 2003/0044868 A1 * | 3/2003 | Aslamkhan et al. | 435/7.92 |
| 2004/0038333 A1 * | 2/2004 | Randolph et al. | 435/68.1 |

FOREIGN PATENT DOCUMENTS

| | | | |
|---|---|---|---|
| DE | 197 30 132 A1 | 2/1999 | |
| EP | 0861 900 A1 | 9/1998 | |
| WO | WO 98/33069 | 7/1998 | |
| WO | WO 00/29850 | 5/2000 | |
| WO | WO 00/36418 | * 6/2000 | |

OTHER PUBLICATIONS

"Application of Prionics Western Blotting Procedure to Screen for BSE in Cattle Regularly Slaughtered at Swiss Abattoirs," from Archives of Virology, Suppl. 16: 189-195. (2000).
International Search Report for PCT/US02/36803 mailed Apr. 15, 2003.
Oesch, B, et al., "Application of Prionics Western Blotting Procedure to Screen for BSE in Cattle Regularly Slaughtered at Swiss Abattoirs." Archives of Virology, 2000, vol. 16, supplement, pp. 189-195.
International Search Report for PCT/US02/36703 filed Nov. 14, 2002, mailed Mar. 31, 2003.
International Search Report for PCT/US02/36803 filed Nov. 14, 2002, mailed Apr. 15, 2003.
International Search Report for PCT/US02/36452 filed Nov. 14, 2002, mailed May 30, 2003.
International Search Report for EP 02793927.1 filed Jun. 14, 2004, mailed Jan. 26, 2005.

* cited by examiner (Continued)

*Primary Examiner*—Long V. Le
*Assistant Examiner*—Gary W. Counts
(74) *Attorney, Agent, or Firm*—Wallenstein Wagner & Rockey, Ltd.

(57) ABSTRACT

Assays are provided for rapid detection, with high specificity of the pathogenic form of prion protein responsible for neurodegenerative diseases affecting humans and animals, such as transmissible spongiform encephalopathy in bovine, sheep, and cats. Also provided are assays for testing animal feedstock, such as animal feed, for the presence or concentration of pathogenic prion protein. Results are available in from about 0.5 to about 20 minutes and preferably within from about 5 to about 10 minutes. The assays employ proteinase-K to remove normal prion protein from a biological sample, so that the sample may be analyzed by immunochromatography to determine the presence and concentration of pathogenic prion protein. Because the proteinase-K is immobilized on a solid support for in situ removal of interfering components, the present invention obviates the need for subsequent extraction of the desired analyte. All aspects of the present invention are suitable for quantifying the minimal detectable amount of pathogenic prion protein in a biological sample. Moreover, the simplicity of sample preparation makes the present invention suitable for use in the field.

34 Claims, 2 Drawing Sheets

RAPID PRION-DETECTION ASSAY

TECHNICAL FIELD

This invention relates to rapid diagnostic assays for testing for disease in animals and humans, and more particularly to assays for detecting the pathogenic form of prion in biological fluids and tissues obtained from animals and humans suspected of having a prion-caused disease as well as foodstuffs made from such biological fluids and tissues.

BACKGROUND OF INVENTION

Humans and animals develop a variety of transmissible neurodegenerative disorders as a result of infection by prions—aberrant proteins that join bacteria, viruses, and viroids as infectious pathogens. Examples of prion diseases afflicting animals include scrapie in sheep and goats, and bovine spongiform encephalopathy (BSE) in cattle. Animals may contract a prion disease by consuming feed made from organs and other components from infected animals, such as cow udders and bone in the form of bone meal. Humans are subject to four prion diseases including kuru, Creutzfeldt-Jakob disease, Gerstmann-Strassler-Scheinker disease, and fatal familial insomnia. Humans may contract Creutzfeldt-Jakob disease by consuming beef, as an example, infected with prions.

A conformational change that occurs in the normal host prion protein causes prion diseases by converting the normal prion protein into an abnormal aggregate-forming pathogenic structure known as a prion. The pathogenic form of prion protein is designated as "$PrP^{SC}$"; the normal form is designated as "$PrP^C$."

Detection of prions is difficult because of the poor solubility of prions in many biological buffers and the tenacity of its aggregates in resisting dissolution. As a result, the methodology used for analyzing prions is oftentimes time-intensive and complex. For example, hydrophilic-interaction chromatography has been used to purify the abnormal prion protein, followed by capillary electrophoresis immunoassay for detection. Schmerr and Jenny, Electrophoresis 19:409 (1998), cited in U.S. Pat. No. 6,150,172.

Despite these problems, however, various assays are known in the art for selectively detecting abnormal prion protein. Among the immunoassays for determining prion protein are techniques such as radioimmunoassay, ELISA (enzyme-linked immunosorbant assay), immunoradiometric assays, gel diffusion precipitation reactions, immunodiffusion assays, in situ immunoassays (using colloidal gold, enzyme or radioisotope labels), Western blots, precipitation reactions, agglutination assays (e.g., gel agglutination assays and hemagglutination assays), complement fixation assays, immunofluorescence assays, protein A and protein G assays, and immunoelectrophoresis assays.

Immunochromatographic assays are known for their ability to analyze proteins. For example, U.S. Pat. No. 6,180,417, issued to Hajizadeh et al., discloses an immunochromatographic assay, featuring both "sandwich" and competitive formats. U.S. Pat. No. 4,703,017 issued to Campbell et al. and U.S. Pat. No. 5,591,645 issued to Rosentein use visible particles in immunochromatography test strips. The test strip and assay of these patents, however, do not provide for the extraction and rapid analysis of pathogenic prion protein.

In U.S. Pat. No. 6,214,565, Prusiner et al. disclose a time- and labor-intensive assay for isolating and detecting the infectious prion protein in materials from human, bovine, sheep, goat and other animals. The assay involves treating a homogenized sample with a protease to remove substantially all non-infectious prion protein. The prion in the treated sample is then crosslinked to a plastic support. The filter is next immersed and incubated in an antibody-containing solution, followed by removal of the unbound antibody. The immersion/incubation/antibody-removal step is repeated with a second solution containing an anti-Ig antibody, typically radiolabled. Results are determined by immunoblot detection, using X-ray film. Conservatively, the assay takes at least four hours to prepare the filter for immunoblot detection.

U.S. Pat. No. 6,150,172 issued to Schmerr et al. discloses a three-step method for extracting abnormal prion protein from homogenized biological material and analyzing the extracted protein with a chromatographic immunoassay. The extraction method includes incubating an aqueous preparation of the biological sample with a pre-measured amount of proteinase-K to digest the normal prion protein, isolating the pathogenic prion protein by mixing the pre-treated sample with an extraction solvent, and recovering the isolated pathogenic prion protein in the extraction solvent. Col. 4, lines 21–26. The method shortens the extraction time to 1 to 2 hours. Col. 9, lines 27–28.

Schmerr et al. disclose that the extraction solvent can then be applied directly to a support and assayed via immunochromatography. The following U.S. patents set forth examples of immunochromatographic assays, known in the art, that may be used for assaying the extraction solvent: U.S. Pat. Nos. 5,248,619; 5,451,504; 5,500,375; 5,624,809; and 5,658,801. Though the referenced method isolates and detects abnormal prion protein, it involves multiple steps and requires as much as two hours for merely extracting the analyte.

Thus, there exists a need for a device and simplified assay for rapidly determining the presence and/or concentration of pathogenic prion proteins in biological samples and animal feed. There also exists a need for test devices and assays that are capable of detecting nanogram quantities of pathogenic prion proteins, particularly, for example, for detecting prion diseases in medical applications and bovine spongiform encephalopathy in animal feed and animal carcasses in the meat-processing industry.

SUMMARY OF THE INVENTION

The present invention is an assay for determining the presence and concentration of pathogenic prion protein in a biological sample obtained from a human or an animal. In each aspect of the invention, the pathogenic form of prion protein is readily extracted, essentially free of the normal nonpathogenic form of prion protein, and analyzed by immunochromatography. Removal of interfering constituents is achieved by treating the sample with proteinase-K, which digests substantially all the nonpathogenic prion protein in the sample.

A first aspect in accordance with the invention is an assay for detecting pathogenic prion in a biological sample. The assay includes homogenizing a biological sample from an animal or a human with a buffer and providing a test device. The test device has proteinase-K immobilized on a support, a membrane in fluid communication with the proteinase-K support, and a pair of antibodies specific to the pathogenic prion protein. The antibodies include one antibody being immobilized on the membrane and the other antibody being labeled for forming a complex with the pathogenic prion protein such that the complex migrates through the membrane toward the immobilized antibody. When the homogenized sample is applied to the test device, the proteinase-K removes substantially all interfering constitutes, such as the noninfectious prion protein. The homogenized sample substantially free of nonpathogenic prion protein migrates through the membrane by capillary action. The pathogenic prion protein present in the sample binds with both antibodies to produce a response in the test strip. The response is interpreted to indicate the presence or concentration of pathogenic prion protein in the sample.

In a second aspect of the invention, an assay is provided for detecting the presence of pathogenic prion protein in a biological sample. The assay comprises preparing a sample for analysis by, e.g., homogenizing the sample with a suitable buffer. A test device is provided for the analysis. The test device has (i) a digestive pad having proteinase-K immobilized therein for removing nonpathogenic prion protein from the biological sample; (ii) a conjugate pad having a labeled first antibody of an antibody pair to the pathogenic prion protein; and, (iii) a test strip having an immobilized second antibody of the antibody pair for producing a response indicative of the presence or concentration of the pathogenic prion protein. The conjugate pad is disposed between the digestive pad and the test strip such that at least a portion of the conjugate pad is in fluid communication with at least a portion of both pads. When the prepared sample is applied to the test device, it flows laterally through the test device. It is first treated with proteinase-K, which digests substantially all of the nonpathogenic prion protein, and then immunochromatographically analyzed. During the immunochromatographic phase, the pathogenic prion protein in the sample binds with both antibodies to produce a response. The response is interpreted to indicate the presence or concentration of prions in the sample.

In a third aspect of the invention, an assay is provided for detecting the pathogenic prion protein in foodstuffs. The assay includes preparing a sample of foodstuff for analysis and providing a test device. The test device has (i) proteinase-K, (ii) a membrane through which the sample migrates by capillary action, the membrane being in fluid communication with the proteinase support; and (iii) a pair of antibodies specific to the pathogenic prion protein including an antibody immobilized on the membrane and a labeled antibody. The prepared sample is applied to the test device for enzymatic treatment and immunochromatographic binding of the pathogenic prion protein. A response, produced by the binding, is interpreted to indicate the presence or concentration of pathogenic prion protein in the antibody.

In yet another aspect of the invention, an assay is provided for detecting pathogenic prion protein in animal foodstuffs. The assay comprises removing interfering constituents from a foodstuff sample by contacting the sample with proteinase-K immobilized on a support. The sample is applied to a test device having (i) a membrane; (ii) an antibody immobilized on the membrane; and (iii) a labeled antibody that complexes with pathogenic prion protein in the sample and migrates through the membrane toward the immobilized antibody. A result, obtained by the immunochromatographic binding of the antibodies to the analyte, indicates the presence or concentration of pathogenic prion protein in the foodstuff.

A final aspect of the invention is an assay for analyzing pathogenic prion protein in biological materials. Relative to other aspects of the invention, this assay eliminates the proteinase-K pretreatment step and utilizes antibodies having particularly high affinity for pathogenic prion protein. The assay comprises extracting prion protein from a biological sample into an aqueous buffer. The prion protein-containing buffer is then applied to a test device. The device includes (i) a membrane through which the homogenized sample migrates by capillary action, the membrane being in fluid communication with the proteinase support; and (ii) a pair of antibodies with high affinity to pathogenic prion protein, including a labeled first antibody and a second antibody that is immobilized on the membrane. Each of the antibodies is specific to a different epitope of the pathogenic prion protein. The pathogenic prion protein in the sample is allowed to bind with both antibodies to produce a test result. The response is interpreted to indicate the presence or concentration of the pathogenic prion protein in the sample.

In all aspects of the invention, a test result is produced within from about 0.5 to about 20 minutes and preferably within about 5 to about 10 minutes. The assay has application in analyzing prion protein responsible for a number of prion-caused diseases in both animals and humans, such as transmissible spongiform encephalopathy (TSE) in bovine, sheep, and goats and Creutzfeld-Jakob-disease (CJD) in humans. Because of the simplicity of sample preparation and analysis, the assay is especially suitable for use in the field; e.g., in both industrial meat processing and medical applications.

BRIEF DESCRIPTION OF THE DRAWINGS

To understand the present invention, it will now be described by way of example, with reference to the accompanying drawings in which.

DETAILED DESCRIPTION OF THE INVENTION

While this invention is susceptible of embodiments in many different forms, preferred embodiments of the invention are illustrated in the drawings and described in detail herein, with the understanding that the present disclosure is to be considered as an exemplification of the principles of the invention and is not intended to limit the broad aspect of the invention to the embodiments illustrated.

The present invention is directed to testing devices, systems, and methods that utilize immunochromatography for determining the presence and concentration of pathogenic prion protein in a biological sample. The present invention utilizes immobilized proteinase-K (PK) enzyme for in-situ removal of interfering components. The devices, systems, and methods are suitable for quantifying the minimal detectable amount of pathogenic prion protein in a biological sample. Moreover, the rapid detection of pathogenic prion protein with high specificity, combined with the simplicity of preparing the sample, makes the present invention suitable for use in the field.

The test devices, systems, and methods may be used for rapid detection of prion diseases such as scrapie and spongiform encephalopathy in bovine, sheep, cats, and other animals. Additionally, the devices, systems, and methods may be used by the medical community for analysis of human tissue for kuru, Creutzeldt-Jakob disease, Gerstmann-Straussler-Scheinker disease and fatal familial insomnia.

Throughout this application, the following terms have the meanings set forth below.

"Biological material" or "biological sample" refers to fluid or tissue extracted from vertebrates, such as brain tissue, whole blood, serum, plasma, saliva, urine, and cerebral spinal fluid.

"Label" refers to a component or "tag" that is attached covalently to a protein of choice. The label could be from a number of detectable groups such as enzymes, visible particles, nanoparticles, and fluorescent components, as examples.

"PrP$^C$" refers to the nonpathogenic form of prion protein, which is enzymatically removed from the biological sample.

"PrP$^{SC}$" refers to the pathogenic prion protein, which is the analyte in the methods of this invention.

Sample Preparation

The present methods, test devices, and systems are used with a biological material extracted from an animal or human. Samples of brain tissue, including organs, are extracted post-mortem; but other samples—such as urine, whole blood, serum, and plasma—may be obtained from the live animal or human. The sample tested may include, e.g., animal feeds, as such items are traditionally made with animal parts such as bovine udders, bone meal, and other organs.

The biological sample is homogenized with a suitable quantity of buffer formulated to optimize the extraction of prion protein into the buffer medium. Homogenization may be accomplished by any technique known in the art, including, e.g., shaking the biological material with weights, vortexing the material, ultrasonic digestion, or comminuting the sample in a homogenizer. Preferably, however, homogenization is conducted by either vortexing or shaking the material with weights.

The buffer does not have organic solvents. Typically, the buffer is an aqueous solution formulated to have an ionic strength of from about 200 to about 400 mM to facilitate prion extraction from the sample. The buffer comprises at least one emulsifier or surfactant, casein, at least one polysaccharide such as a sugar, albumin such as bovine serum albumin (BSA), and a sufficient quantity of water to form a mixture. Typically, the emulsifiers include at least one emulsifier or surfactant such as octoxynol (e.g., IGEPAL$^R$), nonoxynol, polyglycol ether (e.g., Tergitol$^R$ NP), polyoxythylene (10) isooctylphenyl ether, sodium dodecyl sulfate (SDS), or sodium deoxycholate, as examples. A preservative may be used; e.g., ethylene-diamine-tetraacetic acid (EDTA) and sodium azide. The polysaccharides include at least one of sucrose, mannose, trehalose, maltose, and other suitable polysaccharides, as examples, in amount sufficient to yield a molar concentration ranging from about 60 to about 80 mM. Additionally, the buffer may contain a denaturing compound such as guanidine hydrochloride, urea, and guanidine isothiocyanate. The buffer may also contain a zwitterionic buffering salt, such as 4-(2-hydroxy-ethyl)-1-piperazineethane-sulfonic acid (HEPES), used at a concentration ranging from about 1.5 to about 5%, by weight, to maintain the integrity of the solid support for the enzyme used downstream in the analysis.

The total concentration of the emulsifiers and surfactants ranges from about 0.05 to about 5%, by weight of the buffer, and the casein generally ranges from about 10 to about 40%, by weight of the buffer. The total concentration of the polysacccharides ranges from about 0.1 to about 30%, by weight of the buffer. The albumin is typically used at a concentration ranging from about 0.5 to about 4%, by weight of the buffer. The zwitterionic buffering agent may used at a concentration ranging from about 2 to about 5%, by weight. The denaturing agent may be present at a concentration ranging from about 0.1 to about 1 M.

An example of a suitable buffer is shown in Table 1.

TABLE 1

Example of a Buffer Formulation for Extracting Prion Protein.

| Buffer constituent | Concentration (wt %) |
| --- | --- |
| octoxynol | 0.1 |
| casein | 40.0 |
| HEPES | 3.0 |
| EDTA | 0.2 |
| trehalose | 0.1 |
| sucrose | 18.5 |
| BSA | 1.0 |
| NaCl | 1.5 |
| sodium deoxycholate | 0.5 |
| SDS | 0.4 |
| water | 34.7 |

The homogenate is prepared by homogenizing the biological sample with buffer in a weight/volume ratio of sample (mg) to buffer (ml) ranging from about 2:1000 to about 200:1000, and preferably from about 5:1000 to about 100:1000. Most preferably, the ratio of sample (mg) to buffer (ml) is about 30:1000 to about 70:1000.

A. The Test Device

Single, Composite Unit

Figure 1:
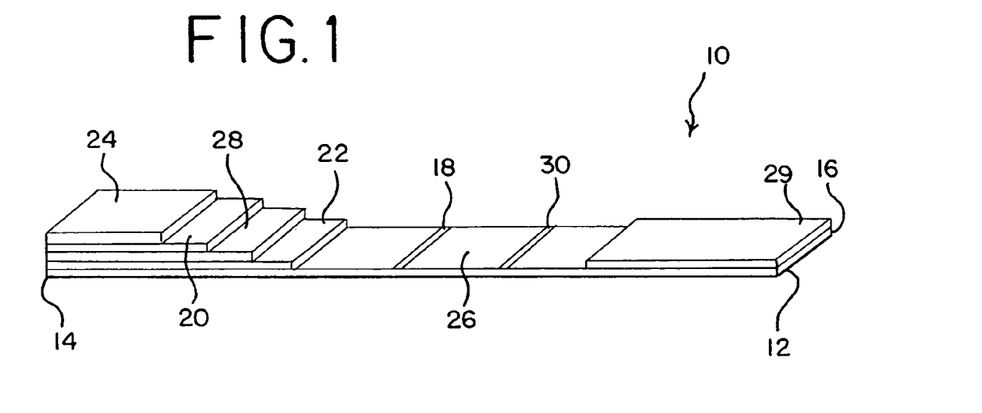
FIG. 1 is a side perspective view of one embodiment of a test device in accordance with the teachings of the present invention.

Shown in FIG. 1 is a test device 10 of a first embodiment. The test device 10 utilizes a pair of antibodies specific to PrP$^{SC}$. These include (1) a labeled antibody that "detects" the PrP$^{SC}$ and (2) an immobilized antibody that "captures" the prion protein-antibody-label complex to form a "sandwich." Briefly, in this invention, homogenized sample of a biological material is introduced to the test device. In the preferred embodiment, the sample first moves through a zone containing immobilized proteinase-K, which digests the nonpathogenic prion protein, leaving the PrP$^{SC}$ for analysis. The proteinase-K is immobilized to a solid support. The removal of the normal prion protein minimizes sample interference and results in a higher specificity for the analyte. As the treated sample moves through the test device, it encounters the first specific antibody conjugated to a label and affixed to a portion of the test device. In one embodiment, the label is a colored latex bead.

The fluid in the homogenized sample re-suspends the antibody-label conjugate so it is free to move through the device. As the antibody-label conjugate moves through the membrane, the labeled antibody binds to a particular epitope of the PrP$^{SC}$ to form a prion protein-antibody-label complex. Via capillary force, the labeled complex migrates through the porous membrane of the device until it reaches the second specific antibody. This antibody is immobilized on the membrane, typically in the form of a band or stripe. The second antibody binds to the second epitope of the PrP$^{SC}$ to which it is specific, resulting in the analyte becoming "sandwiched" between the two antibodies. The resulting "sandwiched" PrP$^{SC}$ produces a detectable change in the membrane, such as the formation of a colored test line, which indicates a positive result. In the absence of antigen, no "sandwich" complex forms and no test line appears.

In an alternative embodiment, the test strip may include more than one "capture" antibody, each applied in a separate test line with each test line being specific to a different prion disease, so that the test device may be used for screening purposes.

The test device 10 includes a test strip 12 having an anterior end 14, a distal end 16, and a "test line" 18 therebetween. The test strip 12 comprises an absorbent material having pores (not shown) ranging from about 10 to about 1000 microns, and preferably from about 10 to about 100 microns. The pores are generally of a size sufficient to allow the homogenized sample, including the re-suspended labeled antibody and conjugates formed by the labeled antibody binding with prion proteins, to migrate laterally through the test strip 12 toward the test line 18.

The test strip itself has at least one layer of absorbent material. Suitable materials include at least one of, e.g., nitrocellulose, cellulose, glass fiber, bonded glass fiber, polyesters, nylon, polyethylsulphone, and other materials having absorbent properties, all of which allow an aqueous sample applied at one end of the test strip to migrate to the opposite end by capillary action.

Although FIG. 1 shows the nitrocellulose membrane or test strip 12 as being rectangular in shape, the test strip, of course, may have virtually any shape that allows an analyte to travel from a point where the sample is introduced to a point where the analyte is detected. Accordingly, the test strip may be square, triangular, circular, or octagonal, or any other suitable shape.

Figure 2:
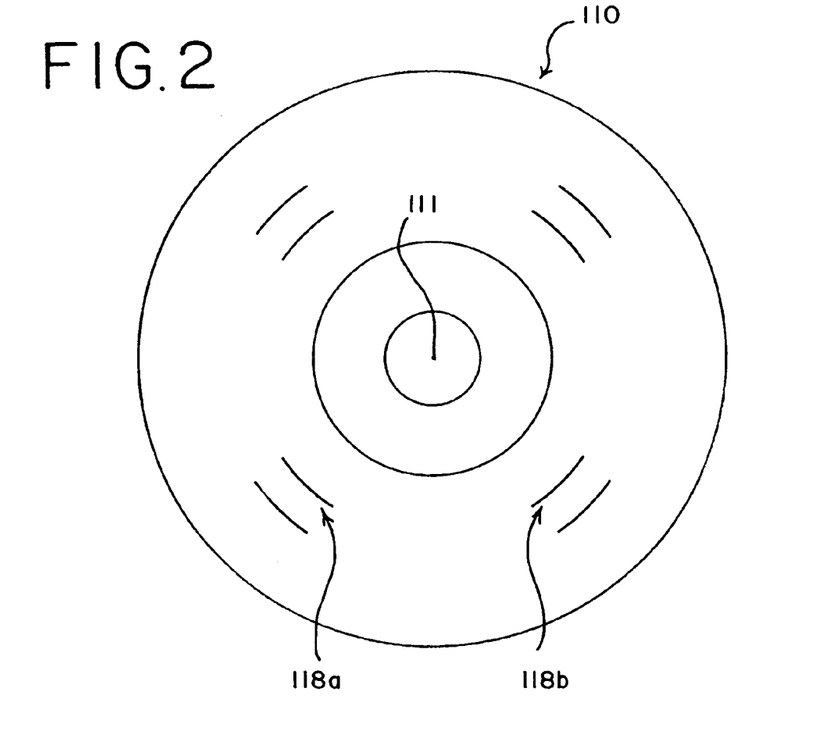
FIG. 2 is a top perspective view of another embodiment of a test device in accordance with the invention.

FIG. 2 shows the test device 110 having a circular configuration, with the immobilized antibody being affixed at a predetermined distance from the sample-introduction site 111. The embodiment shown in FIG. 2 has antibodies for two prion diseases and thus allows the respective pathogenic prion proteins to be analyzed for these in the same test device. Test lines 118a,b each have immobilized antibodies corresponding to the pathogenic prion protein of a different prion disease which allows the device to be used as a diagnostic tool. Any of the test devices, irrespective of their shape, may be used to analyze more than prion disease at the same time.

In a preferred embodiment, the test strip 12 is affixed to a strip support 13 of a sufficiently rigid, impervious and non-reactive material such as polystyrene, polyvinyl chloride, and polyethylene terephthalates. Typically, the strip support is hydrophobic in nature to ensure that the maximum amount of test sample is directed for analysis. In a preferred embodiment, the strip support includes at least one layer of an impervious material.

In yet another embodiment, the entire test strip, and ancillary components described below, may be at least partially encased in a device holder for protecting the device from the environment. This form of the test device is best suited for use in more demanding test environments such as slaughterhouses.

At or near the anterior end 14 of the test strip 12, shown in FIG. 1, is a digestive pad 20 comprising immobilized proteinase-K for digesting nonpathogenic prion protein present in the homogenized biological sample. The digestive pad 20 is generally an absorbent material such as gauze but may comprise other suitable materials such as a plastic filter bed in glass fiber, polyester, and plastic bonded glass fiber, as examples.

The proteinase-K may be bound covalently to the digestive pad or conjugated to a solid support (not shown) impregnated in the digestive pad. The solid support may be, e.g., latex beads, rod-shaped bodies coated with latex, micro- or nanoparticles, beads coated with a dye or a fluorescent or chemiluminescent compound, or a porous membrane pad. Additionally, the proteinase-K may be incorporated into the digestive pad in a gelled substance contained therein. The latex beads in the digestive pad have an average diameter of from about 1 to about 10 microns.

The amount of enzyme on the support medium usually ranges from about 30 micrograms to about 400 micrograms and preferably from about 100 micrograms to about 350 micrograms. The amount of enzyme used should be sufficient to substantially digest all $PrP^c$ present in the sample; typically, this amount is at least 30 units of enzyme per mg of all protein present in the sample. The enzyme treatment is conducted for a time and at a temperature sufficient for the proteinase-K to digest the nonpathogenic prion protein. Generally, digestion is completed in about 2 to about 15 minutes, depending upon the amount of prion present, when conducted at temperatures ranging from about 25° C. to about 60° C.

A conjugate pad 22 is disposed between the digestive pad 20 and the test strip 12, generally near the anterior end 14 of the test strip 12, and is impregnated with a label—typically a particulate—conjugated to one of the antibodies specific to the $PrP^{SC}$. As noted above, the particulates function as labels on the antibodies, allowing easy detection downstream on the nitrocellulose membrane. Suitable particulates for conjugation with the antibody include latex beads, rod-shaped bodies coated with latex, particles comprising a dye, colloidal particles, metal particles, micro- and nanoparticles, fluorescent compounds, chemiluminescent compounds, and magnetic beads, as examples. In one embodiment, the particulates are latex beads filled or coated with a dye, such as blue latex beads. The latex beads typically have an average diameter of from about 50 to about 500 nanometers and preferably from about 100 to about 350 nanometers. The magnetic beads have an average diameter of from about 50 to about 350 nanometers and preferably from about 100 to about 300 nanometers.

The conjugate pad comprises any absorbent material or suitable support for the labeled antibodies, such as a plastic filter bed in glass fiber, polyester, plastic bonded glass fiber, and other nonwoven materials, as examples. The conjugate pad lies in direct fluid communication with the test strip.

An alternative embodiment includes a filter pad 24 in fluid communication with the digestive pad 20, opposite the conjugate pad 22. Homogenized sample may be applied to the filter pad 24, an absorbent pad of a material that receives the fluid sample and allows it to flow into the conjugate pad 22. The filter pad 24 may also function to remove larger particles that may interfere with the assay. The filter pad 24 may comprise any suitable material such as gauze, cellulose, cellulose acetate, other polyesters, and other porous membranes, for example. Alternatively, the sample may be filtered in a separate step prior to its introduction to the digestive pad.

Figure 4:
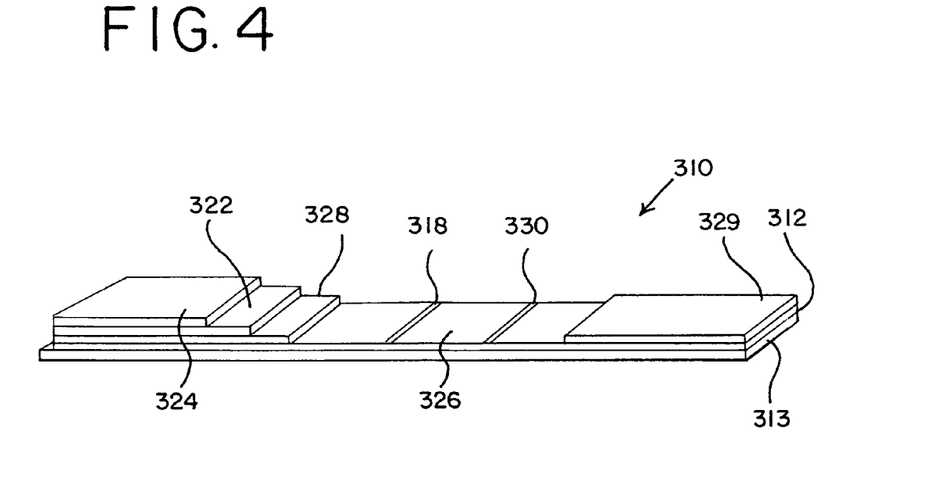

The test device 10 also has a detection region 26 (shown in FIG. 1 and designated by reference numeral "326" in FIG. 4) where the user may view the test result. The detection region 26 includes the test line 18 (shown as "318" in FIG. 4) and the control line 30 (shown as "330" in FIG. 4), when incorporated into the device.

As shown in FIG. 1, the three pads may be layered one atop the other at or near the anterior end, such that the filter pad 24 is the pad farthest from the test strip 12, the conjugate pad 22 is adjacent and substantially aligned with the test strip 12, and the digestive pad 20 is between the filter pad and the conjugate pad.

Figure 3:
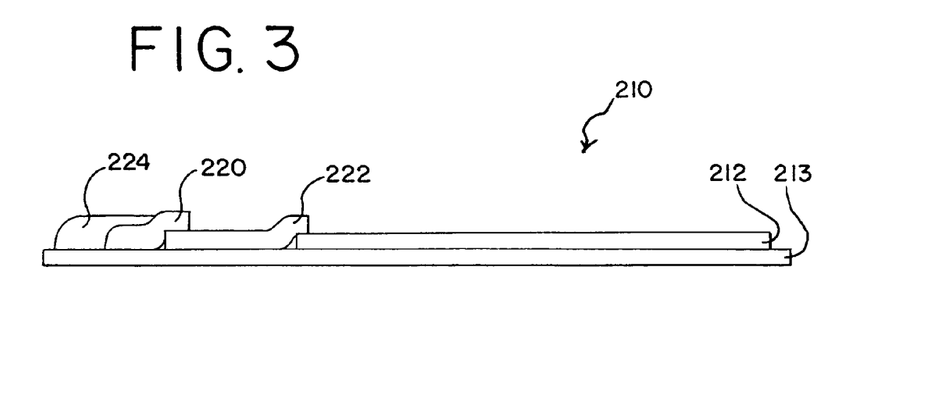
FIG. 3 is a side perspective view of another embodiment of a test device made in accordance with one aspect of the invention; and, FIG. 4 is a side perspective view of still another embodiment of the test device made in accordance with the invention.

In a preferred embodiment of device 210, shown in FIG. 3, the pads lie substantially in the same plane, staggered with respect to each other, so that only a portion of one pad is in contact with a portion of an adjacent pad. Typically, the contact portion is in the form of an overlay between adjacent pads, such that the overlay between adjacent pads and between the conjugate pad 222 and the test strip 212 ranges from about 0.5 to about 5 millimeters and preferably from about 1 to about 2 millimeters. Shown in FIG. 3 are filter pad 224, digestive pad 220, and conjugate pad 222. In the preferred embodiment, at least a portion of each pad and the test strip 212 is adhered to the support 213. The selection, shape, size, and positioning of the pads with respect to each other and the test strip 212 may be optimized as needed. In one embodiment, the pads may be distinct sections of one pad.

The order of the pads may be substantially as set forth above; e.g., the filter pad being the farthest from the detection region, followed by the digestive pad, and then, the conjugate pad. Each pad may have an outer edge generally corresponding in size and shape with that of the other pads, although other configurations are encompassed within the scope of this invention.

An additional pad may be needed to separate digestive pad from the conjugate pad. In another embodiment of the invention, the test strip may have a single pad impregnated with PK enzyme, serving both as the digestive pad and the filter pad. Though optional, this spacer pad 228 may be disposed between the digestive pad 220 and the conjugate pad 222 to allow for more complete digestion of the normal prion before it reaches the conjugate pad.

As shown in FIG. 1, in the detection region 26 lies the second antibody specific to the $PrP^{SC}$, typically immobilized on the membrane in the form of the "test line" or stripe. Alternatively, the antibody may be affixed in any suitable configuration that allows the test result to be viewed, or other wise read, visually or by instrumentation. In another embodiment, the response may be compared against known responses or a standard curve to determine the concentration of the analyte.

In another embodiment, as shown in FIG. 1, the test device 10 includes a wicking pad 29 at the distal end of the test strip 12. The wicking pad 29 promotes the capillary flow of the homogenized fluid sample through the test strip by "drawing" the fluid sample to the distal end.

Generally, the amount of sample introduced to the test device is in the microliter range, typically from about 5 to about 500 microliters and preferably from about 75 to about 150 microliters.

In yet another embodiment, the test device includes a control line for indicating that the test is working properly. The control line, in fixed relation to the test line, comprises an antibody to the labeled antibody, such as immunoglobulin antibody, which binds with labeled antibody to produce a visually detectable line. Alternatively, the control line may be an antibody that binds with a secondary label on the particulate or bead, such as a protein or biotin-avidin binding sites.

The test line is permanent, but it could become visually more pronounced over time. Preferably, the test result is read within from about 2 to about 10 minutes from the time the homogenized sample is applied to the test strip.

The present invention allows pathogenic prion protein to be detected within from about 0.5 to about 20 minutes after sample is introduced to the test device and preferably within from about 5 to about 10 minutes. The invention allows substantially real-time reading of the results on the test strip so that a test result is available almost instantaneously. Therefore, the preferred embodiment of this invention employs enzyme digestion within the test device so that the sample is subjected to only one labor-intensive step; i.e., homogenization. However, when the enzyme pre-treatment is conducted separately from the test strip, detection via the immunochromatographic phase may be yield a readable result in from about 1 to about 5 minutes after sample introduction and preferably from about 2 to about 10 minutes, depending upon the concentration of normal prion protein to be denatured.

Device for Separate Enzyme Pretreatment

The $PrP^{SC}$ may also be detected in biological samples and animal feeds by use of a testing system comprising: (a) proteinase-K immobilized on a support external to the test strip, for digesting the nonpathogenic form of prion protein in a separate wet analysis conducted prior to introducing the homogenized sample to the test strip; and (b) a test strip that analyzes the enzymatically treated sample for the presence and concentration of $PrP^{SC}$. Shown in FIG. 4 is a test device 310, having an impervious strip support 313, that is suitable for use in this aspect of the invention. Test device 310 includes a conjugate pad 322, a detection region 326, and a test line 318. Optionally, the test device may also include one or more of a filter pad 324, a spacer pad 328, a control line 330, and a wicking pad 329. The test system is used with sample prepared as described above.

The test strip—including the antibodies, particulates, conjugate pad, and test line—and its operation are as described above for the device that performs both enzyme treatment and the assay. Additionally, the test strip or membrane may incorporate a control line, described above, for determining whether the test is operating correctly. In this aspect of the invention, the support having the immobilized enzyme separate from the test strip displaces the digestive pad.

The testing system has application, e.g., when the sample must be heated in order to be digested and the PK treatment cannot be performed in real time without heating.

This testing system includes several embodiments. In one embodiment, the support comprises magnetic beads. In an alternative embodiment, the support comprises, e.g., latex supports, filter tips, colloidal particles, microcrystalline particles, conjugate supports, plastic surfaces, and glass surfaces. The latex supports include, e.g., latex beads and latex-coated particles that may be of any shape. The amount of enzyme on the support medium ranges from about 30 micrograms to about 400 micrograms and preferably from about 100 micrograms to about 350 micrograms. The enzyme is used in an amount sufficient to substantially digest all 15' $PrP^{c}$ present in the sample; i.e., at least 30 units of enzyme per mg of all protein present in the sample.

When the sample is mixed with the support in, e.g., a test tube or a beaker, enzymatic digestion of the nonpathogenic prion protein is completed within about 15 minutes. Digestion is typically conducted at temperatures ranging from about 25° C. to about 60° C.

After digestion, the magnetic beads are separated from the mixture with a magnet rack or other suitable device, leaving a supernatant. Other forms of the solid support are removed from the treated sample by in-line filtration or any other suitable method. The supernatant is then applied to the test strip, without requiring further extraction of the prion analyte, for detecting and quantifying the $PrP^{SC}$. As described above, in the presence of $PrP^{SC}$, the test strip undergoes a detectable change, indicative of a positive result.

B. Assay In accordance with the invention, an assay is provided for detecting or quantifying PrP$^{SC}$ in a biological sample and other materials containing biological samples; e.g., animal feedstock such as animal feed. The assay is conducted using test devices and systems as described above. In a first embodiment, the assay is conducted using a lateral flow device or test system where the support for the proteinase-K is in a pad communicating with the test strip, as described above. In this embodiment, the support may be e.g., latex beads, rod-shaped bodies coated with latex, micro- or nanoparticles, beads coated with a dye or a fluorescent or chemiluminescent compound, or a porous membrane pad. Additionally, the proteinase-K may be incorporated into the digestive pad in a gelled substance contained therein.

In a second embodiment, the assay is conducted using a test system or device where the support for the proteinase-K is external to the porous membrane. The support may be, e.g., magnetic beads, latex supports, filter tips, colloidal particles, conjugate supports, plastic surfaces, or glass surfaces.

The first embodiment of the assay includes homogenizing the sample with a suitable buffer, substantially as described above, and applying the homogenized sample to the test device, such as the composite described above and depicted in FIG. 1. The sample may be applied directly to the digestive pad or the filter pad, or it may be filtered onto either of such pads. Preferably, however, filtration is accomplished in situ directly by the device.

In the digestive pad, the homogenized sample is treated with the immobilized proteinase-K. As the homogenized sample and PrP$^{SC}$ flow through the device, the antibody conjugated to a label, such as a colored bead or other particulate, binds the PrP$^{SC}$ to form a labeled complex. By capillary force, the labeled antibody PrP$^{SC}$ complex migrates through the detection zone membrane toward the immobilized antibody where it complexes with the immobilized antibody to produce a visually or otherwise readable response on the membrane, indicative of the presence or concentration of PrP$^{SC}$.

The second embodiment includes homogenizing the sample with a suitable buffer, substantially as described above, and contacting the homogenized sample with a support having immobilized proteinase-K. After the enzyme substantially and preferably completely digests the non-pathogenic form of prion protein, the enzyme-treated sample is applied to a lateral flow device that analyzes the prion protein by immunochromatography. The result, readable either visually or by instrumentation, is correlated to the presence or concentration of the pathogenic prion protein in the sample.

The assay is also suited for detecting the presence of pathogenic prion protein in animal foodstuffs, such as animal feed. In this aspect of the invention, the assay comprises (a) homogenizing a sample of an animal food in a suitable buffer; (b) enzymatically treating nonpathogenic prion protein in the sample with proteinase-K immobilized on a support; and (c) applying the homogenized sample to a test device. The test device is substantially as described above—i.e., it has a porous membrane through which the sample substantially free of nonpathogenic prion protein migrates by capillary action, the membrane being in fluid communication with the proteinase support; and a pair of antibodies specific to the pathogenic prion protein, one of the antibodies being immobilized on the membrane for detecting the pathogenic prion protein; and the other of the antibodies being labeled for forming a complex with the pathogenic prion protein such that the complex migrates toward the immobilized antibody. Analysis proceeds via chromatography, leading to a result indicative of the presence or concentration of pathogenic prion protein in the animal foodstuff.

The enzyme support may be latex beads, rod-shaped bodies coated with latex, micro- or nanoparticles, or a porous membrane pad, as described above. The amount of proteinase-K immobilized on the support is sufficient to substantially digest all protein in the sample, ranging from about 30 micrograms to about 400 micrograms and preferably from about 100 micrograms to about 350 micrograms. The antibodies and labels are as described above.

The buffer used in the homogenizing step facilitates extraction of the prion protein. It comprises at least one emulsifier or surfactant, casein, at least one polysaccharide, salt, albumin, and a sufficient quantity of water to form a mixture. Typically, the buffer is an aqueous solution with an ionic strength of from about 200 to about 400 mM. In the homogenization step, the sample is homogenized with buffer in a weight(mg)/volume(ml) ratio ranging from about 2:1000 to about 200:1000.

A comparison of the intensity of the test line that develops in the presence of the analyte may be used to quantify the amount of analyte in the sample. Such comparison may be made visually, by instrumentation, or by a standard curve using readings taken by instrumentation.

Another embodiment of the invention is an assay for determining the presence or concentration of pathogenic prion protein in a sample of animal feed or biological material obtained from a human or an animal. In this embodiment, the assay eliminates the proteinase-K pretreatment step and may be run utilizing antibodies having particularly high affinity for pathogenic prion protein. The assay comprises homogenizing the sample with a suitable aqueous buffer in the weight:volume ratio described above to extract prion protein. The solvent has an ionic strength ranging from about 200 to about 400 mM. The homogenate is applied to a test device as described above, without the immobilized enzyme. The test device includes a porous membrane through which the homogenized sample migrates by capillary action, the membrane being in fluid communication with the proteinase support; and a pair of antibodies specific to pathogenic prion protein. One antibody is immobilized on the membrane for capturing the pathogenic prion protein, and the other antibody is labeled and forms a complex with the pathogenic prion protein for detecting the pathogenic prion. The complex migrates toward the immobilized antibody, where it is bound, producing a detectable or otherwise readable response. The response indicates the presence or concentration of the pathogenic prion protein in the sample.

The antibodies used in this embodiment possess a high affinity to the pathogenic prion protein, such that they may bind with the epitopes of the prion protein without interference from extraneous materials, such as the noninfectious form of the prion protein. The antibodies may be obtained from Case Western Reserve University, Cleveland, Ohio.

The assays in accordance with the invention allow substantially real-time reading of the results on the test device so that results are available almost instantaneously. The enzymatic digestion of interfering constituents in situ requires the sample to be subjected to only homogenization prior to introduction to the device. However, when the enzyme pre-treatment is conducted separately from the test strip, detection via the immunochromatographic phase may be yield a readable result in from about 1 to about 5 minutes after sample introduction and preferably from about 2 to about 10 minutes, depending upon the concentration of normal prion protein to be denatured. Otherwise, results are available in from about 0.5 to about 20 minutes after the homogenate is introduced to the lateral flow device.

While the specific embodiments have been illustrated and described, numerous modifications come to mind without significantly departing from the spirit of the invention and the scope of protection is only limited by the scope of the accompanying claims.

We claim:

1. An assaying method for detecting a prion disease in an animal or a human, the method comprising the steps of:
   (a) homogenizing a biological sample from an animal or a human suspected of containing a pathogenic prior protein with a buffer comprising:
      (i) at least one surfactant or emulsifier;
      (ii) at least one polysaccharide;
      (iii) casein; and
      (iv) albumin;
   (b) providing a test device comprising:
      (i) a digestive pad comprising immobilized proteinase-K;
      (ii) a membrane through which the homogenized sample of pathogenic prion protein migrates by capillary action, the membrane being in fluid communication with the proteinase-K support; and
      (iii) a pair of antibodies to the pathogenic prion protein, one of the antibodies being immobilized on the membrane, and the other of the antibodies being labeled for forming a complex with the pathogenic prion protein such that the complex migrates toward the immobilized antibody;
   (c) applying the homogenized biological sample to the test device wherein:
      (i) the proteinase-K removes interfering constituents, and
      (ii) the pathogenic prion protein in the sample binds with both antibodies to produce a response; and
   (d) interpreting the response to indicate the presence or concentration of the pathogenic prion protein in the sample.

2. The assay of claim 1 wherein the prion being analyzed causes a condition selected from the group consisting of transmissible spongiform encephalopathy (TSE) in bovine, sheep, and goats; scrapie in sheep and goat; transmissible mink encephalopathy (TME) in mink; chronic wasting disease (CWD) in mule deer and elk; feline spongiform encephalopathy in cats; and kuru, Creutzfeld-Jakob-disease (CJD), German-Straussler-Scheinker syndrome (GSS), and fatal familial insomnia (FFI) in humans.

3. The assay of claim 1 wherein the biological sample is selected from brain tissue, whole blood, serum, plasma, saliva, urine, and cerebral spinal fluid.

4. The assay of claim 1 wherein the emulsifier or surfactant is selected from octoxynol, nonoxynol, polyglycol ether, polyoxyethylene (10) isooctylphenyl ether, sodium dodecyl sulfate, and sodium deoxycholate.

5. The assay of claim 1 wherein the buffer is an aqueous solution with an ionic strength of from about 200 to about 400 mM.

6. The assay of claim 1 wherein the response is read visually.

7. The assay of claim 1 wherein the response is produced within from about 0.5 to about 20 minutes after the sample is applied to the test device.

8. The assay of claim 1 wherein the response is produced within from about 5 to about 10 minutes after the sample is applied to the test device.

9. The assay of claim 1 wherein the interpreting step comprises comparing the response to known responses to determine the concentration of the pathogenic prion protein.

10. An assay for determining the presence or concentration of pathogenic prion protein in a biological sample, the assay comprising:
    (a) preparing a sample for analysis by homogenizing the sample with a buffer comprising at least one surfactant or emulsifier, at least one polysaccharide, casein, and albumin;
    (b) providing a test device having:
       a digestive pad having proteinase-K immobilized therein for removing nonpathogenic prion protein from the biological sample;
       a conjugate pad having a labeled first antibody of an antibody pair to the pathogenic prion protein; and,
       a test strip having an immobilized second antibody of the antibody pair for producing a response indicative of the presence or concentration of the pathogenic prion protein; the conjugate pad being disposed between the digestive pad and the test strip;
    (c) applying the prepared sample to the test device so the sample is treated with proteinase-K and the pathogenic prion protein in the sample binds with both antibodies to produce a response; and
    (d) determining the presence or concentration of the pathogenic prion protein in the sample based on the response.

11. The assay of claim 10 wherein the preparing step comprises homogenizing the sample with a buffer to extract prion protein into the buffer medium.

12. The assay of claim 10 wherein the preparing step comprises extracting prion protein into an aqueous buffer medium.

13. The assay of claim 10 wherein the proteinase-K is immobilized on a support selected from latex beads, rod-shaped bodies coated with latex, micro- or nanoparticles, and a porous membrane pad.

14. The assay of claim 10 wherein the proteinase-K is in a gelled substance contained in the digestive pad.

15. The assay of claim 10 wherein the proteinase-K immobilized on the support digests the nonpathogenic prion protein in the sample.

16. The assay of claim 13 wherein the proteinase-K is immobilized on latex beads.

17. The assay of claim 10 wherein the amount of proteinase-K ranges from about 30 micrograms to about 400 micrograms.

18. The assay of claim 10 wherein the response is read visually.

19. The assay of claim 10 wherein the sample preparing step comprises homogenizing the sample with a buffer in a weight/volume ratio of sample (mg) to buffer (ml) ranging from about 2:1000 to about 200:1000.

20. The assay of claim 10 wherein the sample preparing step comprises homogenizing the sample with a buffer having an ionic strength ranging from about 200 to about 400 mM.

21. The assay of claim 10 wherein the at least one emulsifier in the buffer is selected from octoxynol, nonoxynol, polyglycol ether, polyoxyethylene (10) isooctylphenyl ether, sodium dodecyl sulfate, and sodium deoxycholate.

22. The assay of claim 10 wherein the at least one polysaccharide in the buffer is selected from sucrose, mannose, trehalose, and maltose.

23. The assay of claim 10 wherein the at least one polysaccharide is used at a concentration ranging from about 0.1 to about 30%, by weight of the buffer.

24. The assay of claim 10 wherein the buffer further comprises a zwitterionic buffering agent.

25. The assay of claim 10 wherein the response is read by instrumentation.

26. An assay for detecting the presence or concentration of pathogenic prion protein in foodstuffs, comprising:
   (a) preparing a sample of foodstuff for analysis homogenizing the sample with an aqueous buffer comprising at least one surfactant or emulsifier, at least one polysaccharide, casein, and albumin;
   (b) providing a test device having:
      (i) proteinase-K immobilized on a support;
      (ii) a membrane through which the sample migrates by capillary action, the membrane being in fluid communication with the proteinase support; and
      (iii) a pair of antibodies to the pathogenic prion protein including an antibody immobilized on the membrane and a labeled antibody;
   (c) applying the prepared sample to the test device for immunochromatographic binding of the pathogenic prion protein to produce a response; and
   (d) determining the presence or concentration of the pathogenic prion protein in the sample based on the response.

27. The assay of claim 26 wherein the sample preparing step comprises homogenizing the sample with a buffer in a weight/volume ratio of sample (mg) to buffer (ml) ranging from about 2:1000 to about 200:1000.

28. The assay of claim 26 wherein the sample preparing step comprises homogenizing the sample with a buffer having an ionic strength ranging from about 200 to about 400 mM.

29. The assay of claim 26 wherein the sample preparing step comprises homogenizing the sample with an aqueous buffer to extract prion protein into the buffer medium.

30. The assay of claim 26 wherein the sample is animal feed.

31. An assay for pathogenic prion protein in foodstuffs, comprising:
   (a) preparing a sample of foodstuff for analysis, wherein the sample preparing step comprises:
      homogenizing the sample with an aqueous buffer comprising at least one surfactant or emulsifier, at least one polysaccharide, casein, and albumin;
   (b) removing interfering constituents from a foodstuff sample by contacting the sample with proteinase-K immobilized on a support;
   (c) applying the sample to a test device having
      (i) a membrane; and
      (ii) an antibody immobilized on the membrane; and
      (iii) a labeled antibody that complexes with pathogenic prion protein in the sample and migrates through the membrane toward the immobilized antibody; and
   (d) analyzing the labeled antibody that complexes with the pathogenic prion protein for-the presence or concentration of pathogenic prion protein in the foodstuff.

32. The assay of claim 31 wherein the buffer has an ionic strength of from about 200 to about 400 mM.

33. The assay of claim 31 wherein prior to the constituent-removal step, the sample is homogenized with a buffer in a weight (mg)/volume (ml) ratio ranging from about 2:1000 to about 200:1000.

34. An assay for detecting the presence or concentration of pathogenic prion protein in a sample of biological material, the assay comprising:
   (a) extracting prion protein from a biological sample into an aqueous buffer comprising:
      (i) at least one surfactant or emulsifier;
      (ii) at lest one polysaccharide;
      (iii) casein; and
      (iv) albumin;
   (b) applying the prion protein-containing buffer to a test device having:
      (i) a membrane through which a homogenized sample migrates by capillary action, the membrane being in fluid communication with a proteinase support; and
      (ii) a pair of antibodies with high affinity to pathogenic prion protein, including a labeled first antibody and a second antibody immobilized on the membrane, each of the antibodies specific to a different epitope of the pathogenic prion protein;
   (c) allowing the pathogenic prion protein in the sample to bind with both antibodies to produce a test result; and
   (d) interpreting the response to indicate the presence or concentration of the pathogenic prion protein in the sample.

* * * * *